United States Patent [19]

Gardner, Jr.

[11] Patent Number: 4,833,699
[45] Date of Patent: May 23, 1989

[54] X-RAY FILM POSITIONER

[76] Inventor: John E. Gardner, Jr., 3402 W. Ridge Rd., Roanoke, Va. 24014

[21] Appl. No.: 112,486

[22] Filed: Oct. 26, 1987

[51] Int. Cl.$^4$ ............................................. G03B 42/04
[52] U.S. Cl. ...................................... 378/170; 378/168
[58] Field of Search ............................. 378/168–170, 378/38

[56] References Cited

U.S. PATENT DOCUMENTS

| 1,947,014 | 2/1934 | Levy | 378/170 |
| 4,507,798 | 3/1985 | Welander | 378/168 |
| 4,633,493 | 12/1986 | Linden | 378/168 |
| 4,707,847 | 11/1987 | Van Aken | 378/168 |
| 4,731,808 | 3/1987 | Ogunsunlade | 378/170 |

Primary Examiner—Carolyn E. Fields
Assistant Examiner—Joseph A. Hynds

[57] ABSTRACT

Disclosed is an x-ray film packet positioner device by means of which certain x-ray film views can be obtained and which is especially adaptable to all disciplines of dental practice but not limited to same. This invention consists of two units, namely a positioner body device and an x-ray film packet holding rod device. The positioner body of the invention is stabilized and held in position by a bite platform device and contains slots for positioning and holding x-ray film packets for obtaining certain x-ray film views as well as containing a hole in which a positioner x-ray film packet holding rod device can be placed. The positioner body contains holes into which are inserted retaining devices and by means of which an x-ray film packet holding rod device is stabilized and fixed in position, and by which the body of the invention is tightened against a bite platform. The x-ray film packet holding rod device contains slots for holding x-ray film packets in certain positions. A bite platform device is held steady and in fixed position by the closed engagement contact of the patient's upper and lower front teeth with the positioner.

6 Claims, 4 Drawing Sheets

X-RAY FILM POSITIONER

FIELDS OF SEARCH AND CROSS REFERENCES

The inventor searched U. S. Patent Classifications 378/168 and 170; and 250/478 and 479; and International Patent Classification GO3B41/16. No device was found that resembles the herein described invention.

Related patent references are not cited since no similar device was found on search. The techniques for taking the x-ray film views which the invention permits are adequately described in "Dental Radiology", Third Edition, Wuehrmann and Manson-Hing, published by the C. V. Mosby Company. This invention permits taking x-ray film views of the temporomandibular joint for which there are several devices on the market. However, these devices, such as U.S. Pat. No. 4,455,671, June 19, 1984 in favor of William B. Farrar, the Denar Accurad-100 and 200 and the Updegrave Board, are complicated and require the use of expensive film cassettes and different x-ray film than this invention.

INVENTION SUMMARY

This invention provides a means to now obtain very clear and precise x-ray film views of portions of the upper jaw and especially of the premaxillary portion of the same in the inferior-superior and anterior-posterior aspecs. This is especially important in locating impacted mesiodens for proper diagnosis and in planning the surgical approach for their removal. Unique views of the relatioship of the posterior upper teeth to the floor of and the lower half of the maxillary sinuses can be obtained with this invention.

This invention provides a means to obtain clear and precise views of particular areas of interest of the lower jaw. The positioner holds an x-ray film packet of sufficient size to permit an image on x-ray film of the x-ray target area from the biting surfaces of the teeth to the lower border of the jaw bone. By appropriately positioning the x-ray film packet in either the body of the positioner or the positioner x-ray film packet holding rod device as indicated, x-ray film views can be taken of any portion of the lower jaw from the midline posteriorly to and including the ramus of the lower jaw.

This invention will permit the taking of x-ray film views of the closed position of the temporomandibular joint, its advantage being the simplicity and speed of obtaining the x-ray film views without the need for heavier, more complicated and cumbersome equipment. This is practical in treatment situations where the position of the condyle in the joint fossa is of concern and where an initial x-ray film view is desired and needed to make a decision if further diagnostic radiographic evaluation is indicated.

In addition to providing the above listed advantages in expanded diagnostic capability, this invention facilitates that role by being small, light in weight and non-intimidating; a feature which is most important in dealing with children and frightened adults.

This invention provides an effective means of obtaining immediate x-ray film examination for patients who are known to have, or who are suspected of having, some contagious disease such as AIDS, Hepatitis, or Herpes. Also greatly benefited is the patient whose face or jaw is so swollen or diseased that an intra-oral periapical dental x-ray cannot be obtained when needed. This invention provides a means to obtain needed x-ray film views of these compromised patients and at the same time provides the health professional with some added measure of protection. Protection of patients and health professionals from cross contamination is aided by the ability of the invention to be fully sterilized.

The above advantages in obtaining the x-ray film views extraorally are the result of the novelty of this invention. This invention fulfills its object of providing the capability for expanded diagnostic x-ray film view capability, ease of operation, user protection and economy.

This x-ray film positioner invention consists of a positioner body device and an x-ray film packet holding rod device. Adjunctively it utilizes two retaining devices such as the preferred set screws and a bite platform device. The invention is constructed of metal or any other material of sufficient strength and other property to accomplish its stated object.

DESCRIPTION OF THE DRAWINGS

FIG. 8 is a perspective view of the exemplary body of this invention as shown in FIG. 1 connected to a bite platform which is held fixed between the patient's upper and lower front teeth; the positioner body holding and fixing an x-ray film packet in proper position for taking either a premaxillary or maxillary sinus floor x-ray film view; the x-ray beam emanating source being so positioned as to properly direct the central x-ray beam through the target view area so as to contact the x-ray film packet at its mid-point at the proper angle;

FIG. 9 is a perspective view of the exemplary body of this invention as shown in FIG. 1 connected to a bite platform which is held fixed between the patient's upper and lower front teeth; the positioner body holding and fixing an x-ray film packet in proper position for taking an x-ray film view of the front portion of the lower jaw; the x-ray beam emanating source being so positioned as to properly direct the central x-ray beam through the target view area so as to contact the x-ray film packet at its mid-point at the proper angle;

FIG. 10 is a perspective view of the exemplary embodiments of this invention as shown in FIG. 1; the positioner body device is connected to a bite platform device which is fixed by surface engagement between the patient's upper and lower front teeth; the positioner body contains a hole which contains a portion of the x-ray film packet holding rod device shown inserted through said hole; the x-ray film packet holding rod device holding an x-ray film packet in proper position for taking an x-ray film view of a target view area of a portion of the posterior lower jaw area; the x-ray beam emanating source being so positioned as to properly direct the central x-ray beam through the target view area so as to contact the x-ray film packet at its mid-point at the proper angle;

FIG. 11 is a perspective view of the exemplary embodiments of this invention as shown in FIG. 1; the positioner body device is connected to a bite platform which is fixed by surface engagement between the patient's upper and lower front teeth; the positioner body which contains a hole which contains a portion of the x-ray film packet holding rod device shown inserted through said hole; the x-ray film packet holding rod device holding an x-ray film packet in proper position for taking an x-ray film view of a target view area of the temporomandibular joint; the x-ray beam emanating source being so positioned as to properly direct the central x-ray beam through the target view area so as to contact the x-ray film packet at its mid-point at the proper angle;

FIG. 1 illustrates the presently preferred exemplary embodiment of this invention. It can now be readily appreciated that device size, form, configuration or material which incorporate the features necessary to accomplish the hereinabove stated object can be quite varied.

SPECIFICATIONS AND DETAILED DESCRIPTION

Figure 1:
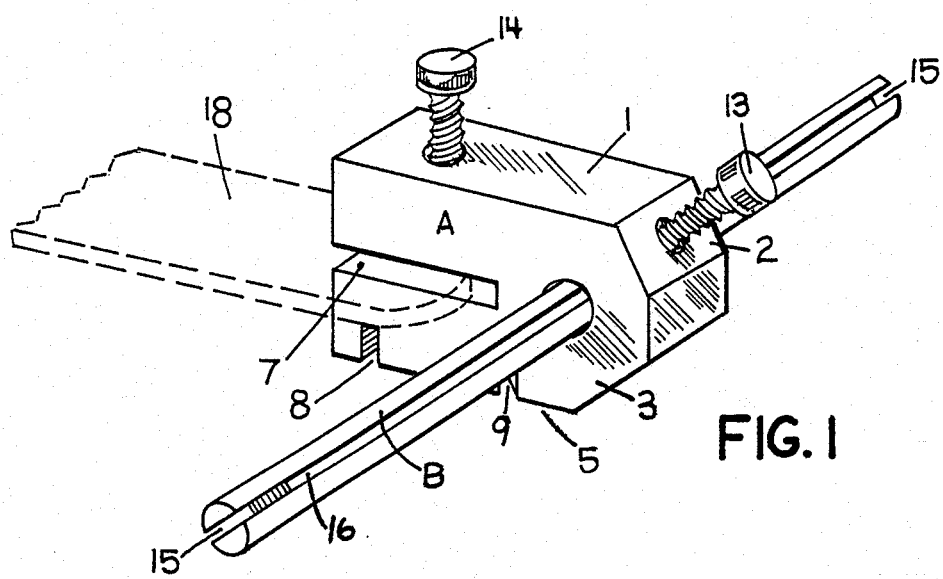
FIG. 1 is a perspective view of an exemplary embodiment of an extra-oral x-ray film positioner device according to the invention.

Attention now focusing on FIGS. 1-7, the exemplary extraoral x-ray film positioner consists of two parts, a positioner body device (A) having a first surface 4 and a second surface 5 and an x-ray film packet holding rod device (B). Adjunctively used with these exemplary embodiments are a bite platform device (18), a bite platform retaining device (14) such as the type of preferred set screw (14) provides first attaching means and an x-ray film packet holding rod retaining device (13) such as the type of preferred set screw (13) provides second attaching means.

Figure 2:
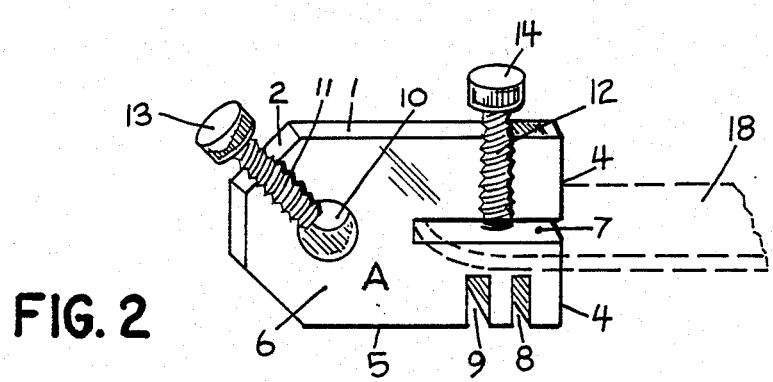
FIG. 2 is a cross sectional view of an exemplary body of the exemplary device shown in FIG. 1 depicting the side on which the x-ray film packet retaining slots are closest together and illustrating the preferred retaining devices being set screws and a bite platform device situated in a bite platform slot.
Figure 3:
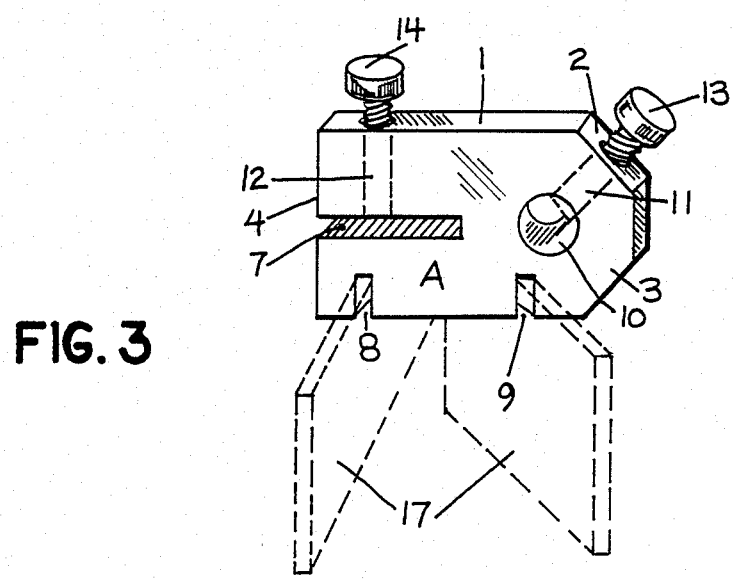
FIG. 3 is a perspective view of an exemplary body of the exemplary device shown in FIG. 1 illustrating the side on which the x-ray film packet retaining slots are furthest apart; and depicting x-ray film packets positioned in saidi slots.
Figure 4:
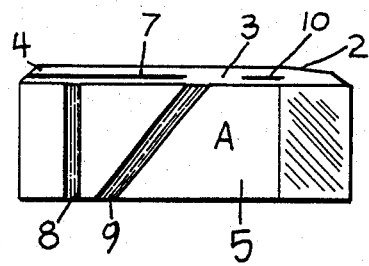
FIG. 4 is a pespective view of the body of the exemplary device shown in FIG. 1 depicting the surface containing the full length and angle of the x-ray film packet retaining slots.
Figure 5:
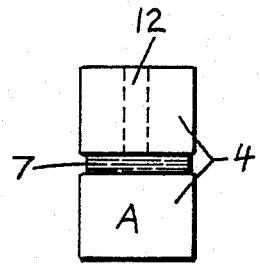
FIG. 5 is a perspective view of the body of the exemplary device shown in FIG. 1 depicting the surface of entrance for a bite platform device.
Figure 6:
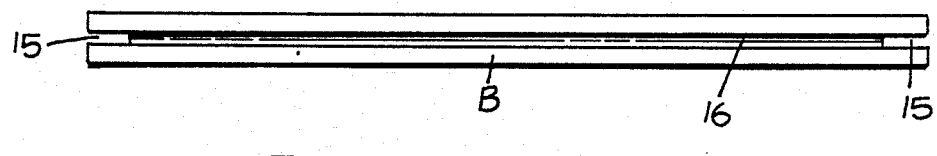
FIG. 6 is a perspective view of an exemplary embodiment of the x-ray film packet holding rod device shown in FIG. 1.
Figure 7:
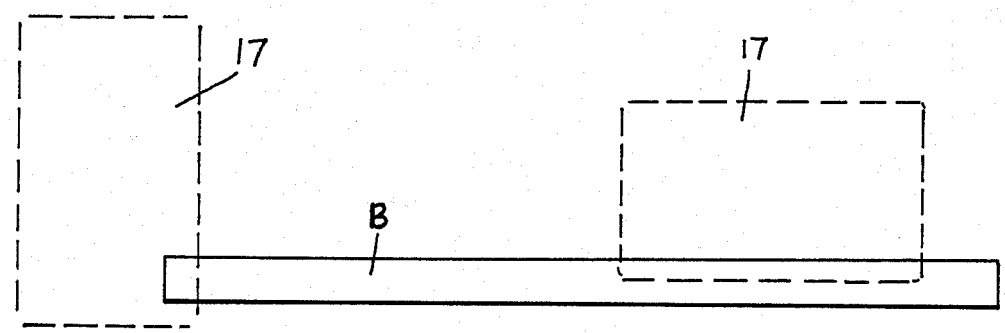
FIG. 7 is a perspective view of an exemplary x-ray film packet holding rod device as shown in FIG. 6 depicting an x-ray film packet inserted into its x-ray film packet retaining slots.

The illustrated preferred exemplary embodiment of the positioner body device (A) consists of a bite platform recess such as the preferred exemplary slot on opening (7) as illustrated in FIGS. 1, 2, 3, 4, 5, by which a bite platform device (18) such as a disposable wooden tongue blade (18) may be inserted and held firmly connected by some means such as a bite platform retaining device set screw (14) which also fixes the desired position of the body of the positioner (A) in relation to the target view area for the particular x-ray film view to be taken. The positioner body device (A) contains a hole (12) illustrated in FIGS. 2, 3, 5, which said hole originates on surface (1) and extends to a bite platform slot (7) as illustrated in FIGS. 2, 3, 5, and said hole (12) contains a bite platform (18) retaining device (14) such as the preferred retaining set screw (14) shown in FIGS. 1, 2, 3. The body of the positioner (A) contains a hole (10) as identified in FIGS. 2, 3, 4, through which an x-ray film packet holding rod device (B) such as the illustrated preferred embodiment of such rod (B) as shown in FIGS. 1, 6, 7, can be placed and adjusted as required. The positioner body device (A) contains a hole (11) illustrated in FIGS. 2 and 3, which said hole originates on surface (2) and extends to the x-ray film packet holding rod device hole (10) as illustrated in FIGS. 2 and 3 and said hole (11) contains an x-ray film packet holding rod (B) retaining device (13) such as the preferred retaining set screw (13) illustrated in FIGS. 1, 2, 3. The x-ray film packet holding rod device (B) is fixed in desired position by the x-ray film packet holding rod (B) retaining device (13) as illustrated in FIG. 1. The preferred embodiment of the body of this positioner device (A) contains on a surface or surfaces x-ray film packet retaining device such as the preferred exemplary slots (8) and (9) of proper dimension and angulation as illustrated in FIGS. 1, 2, 3, 4, and whose function it is to hold in a fixed position suitable x-ray film packets (17) as shown in FIG. 3 for obtaining certain x-ray film views.

The illustrated preferred exemplary embodiment of the x-ray film packet holding rod device (B) is shown in FIGS. 1 and 6 and contains x-ray film packet retaining device such as the preferred exemplary slot (16) of proper dimension contained on a surface or surfaces throughout the entire length, or part of the entire length, of the said x-ray film packet holding rod device (B); and either or both ends (15) of said x-ray film packet holding rod device (B) contain an x-ray film packet retaining device such as the preferred exemplary slot (15) of proper dimension which extends entirely through said x-ray film packet holding rod device (B) end (15) creating complete open-end slots or slits (15), both of which hold suitable x-ray film packets (17) in desired and variable fixed positions as placed therein as illustrated in FIG. 7.

Figure 8:
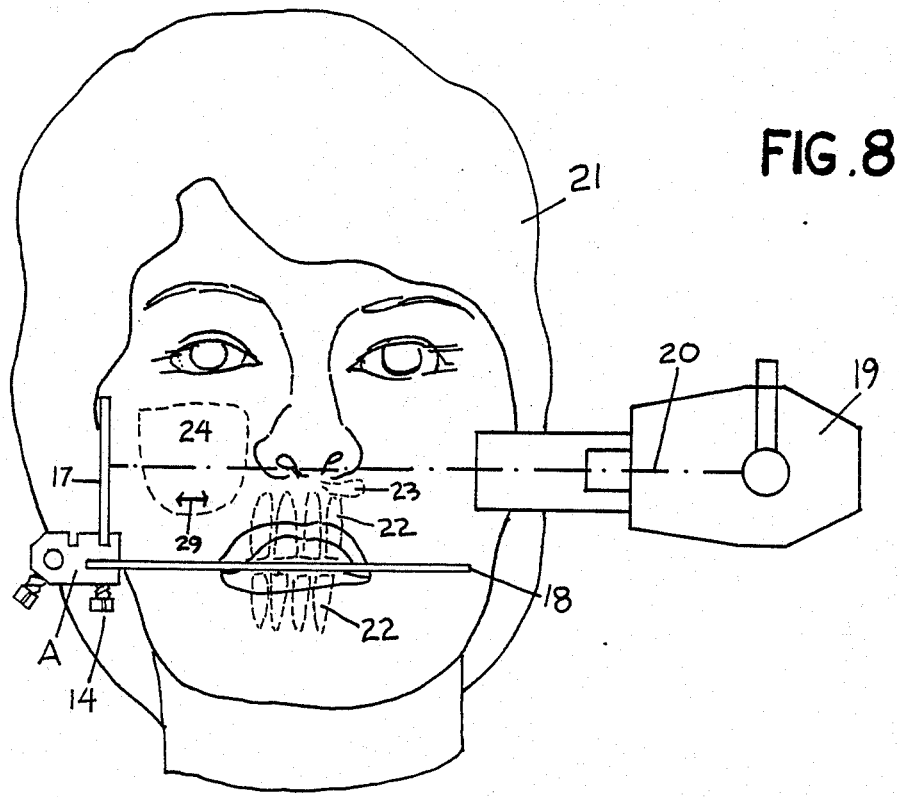
FIGS. 8–11 illustrate the taking of x-ray film views on the right side of a patient. X-ray film views of the left side can be obtained by mirror imaging the right side technique for each respective view.
Figure 9:
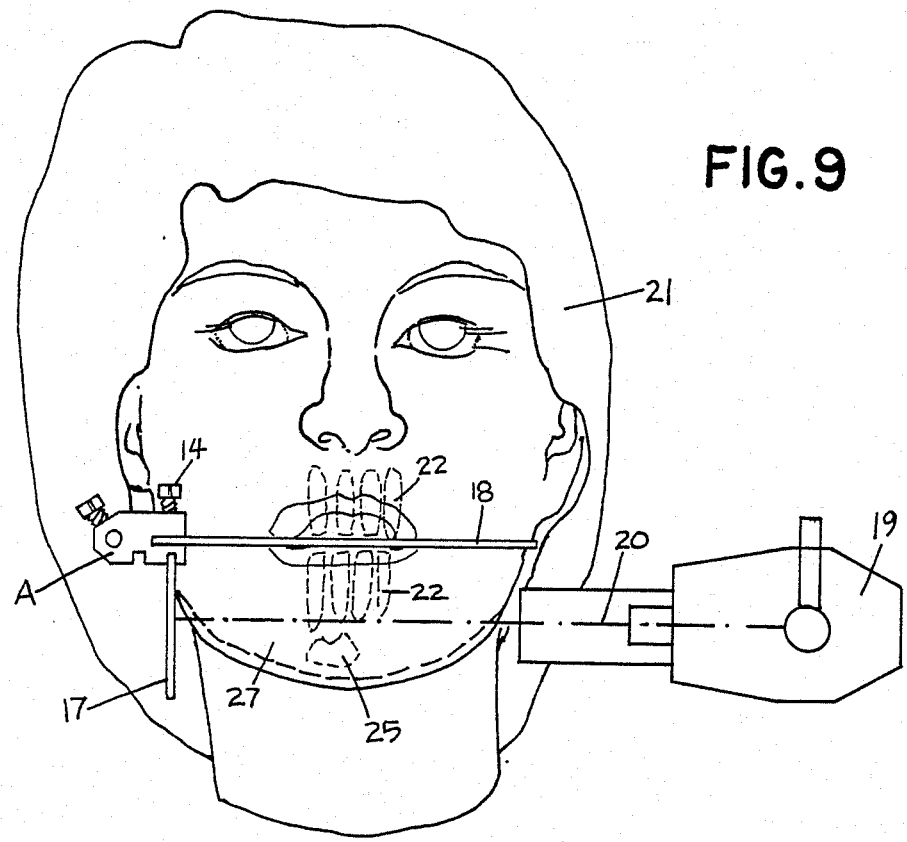
Figure 10:
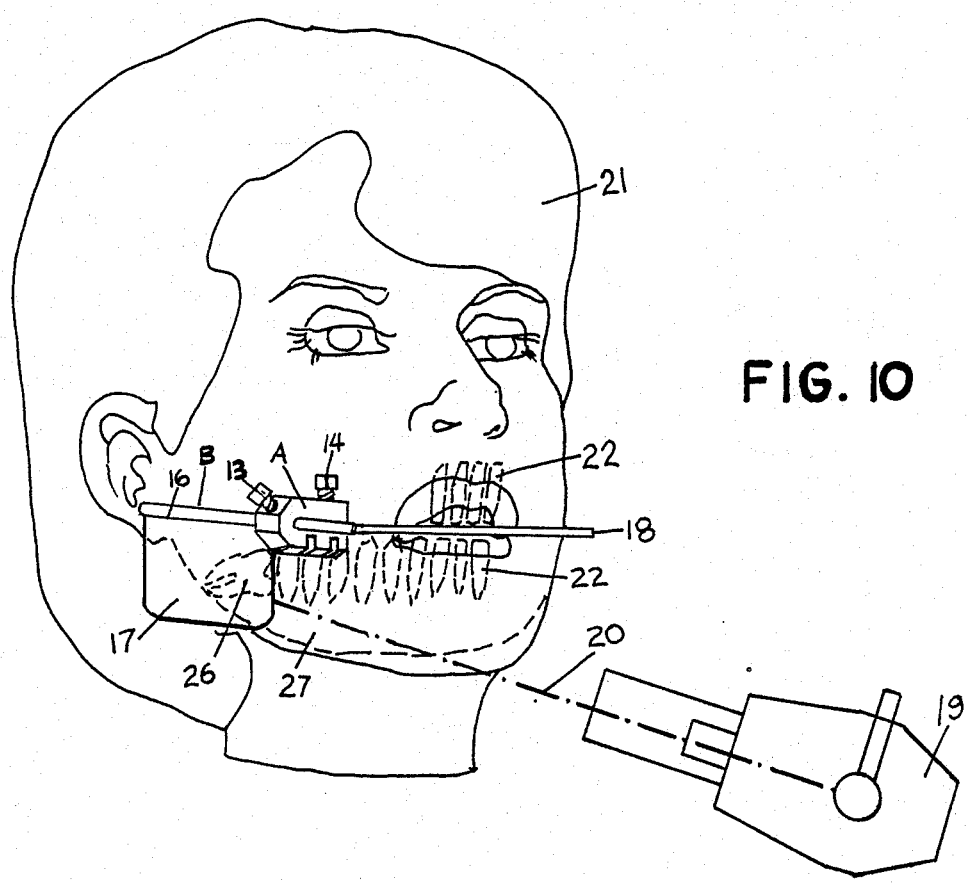
Figure 11:
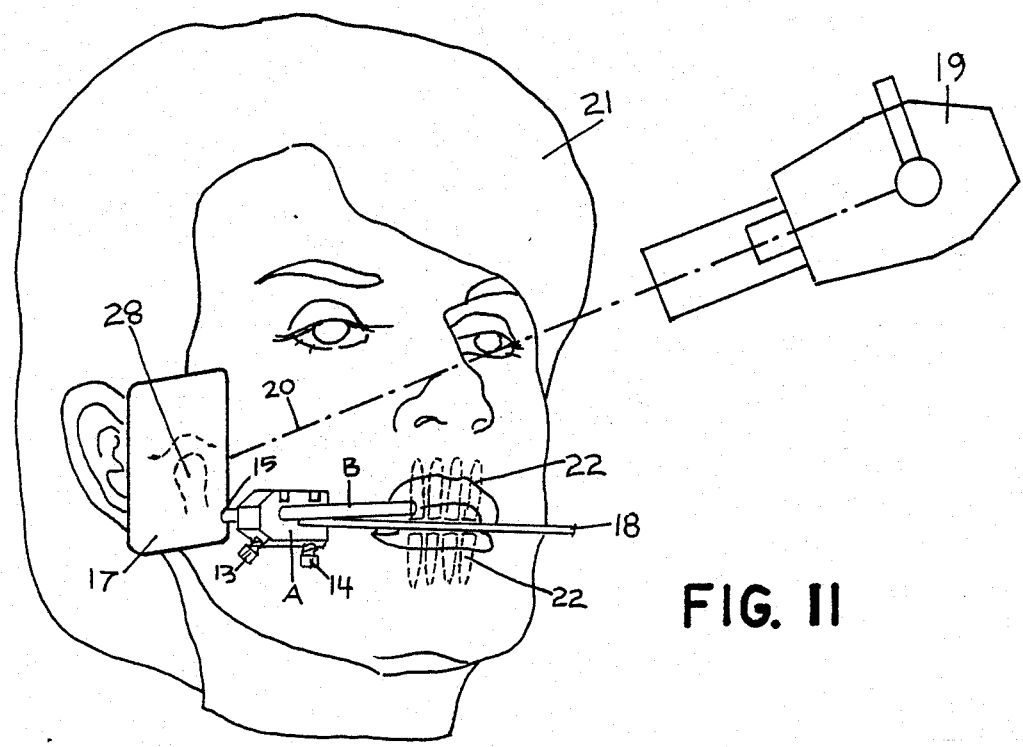

The basic technique for utilizing this invention to obtain x-ray film views as illustrated in FIGS. 8, 9, 10, 11, is by having the patient (21) engage the front upper and lower teeth (22) against their respective surface of a bite platform (18) thereby holding the positioner body (A) steady and in the intended position after engaging the appropriate fixing retaining device such as a bite platform retaining device set screw (14). FIGS. 10 and 11 illustrate the preferred exemplary x-ray film packet holding rod device (B) being held bu the x-ray film positioner body (A) in fixed position by an appropriate retaining device such as the exemplary retaining device set screw (13). This positioner invention may be utilized for the benefit of edentulous persons who possess dentures by engaging the upper and lower denture teeth against the respective surfaces of a bite platform (18). Edentulous persons without dentures may be served by this invention by placing wax bite rims in the mouth and causing the surfaces of the wax bite rims to contact a bite platform surface (18) under jaw closing pressure. Therefore, edentulous patients, with or without dentures, may benefit from this invention by using the herein described x-ray film view techniques.

FIG. 8 illusrates the technique for obtaining the desired x-ray film views of the upper jaw and sinus area

(24) and the floor of the maxillary sinus (29). Referring to the previous paragraph pertinent to basic technique for utilizing the invention, the x-ray views are obtained by placing an x-ray film packet (17) in a proper position in an x-ray film packet retaining device slot (8) or (9) located in the x-ray film positioner body (A) which is then adjusted and fixed in proper position; then directing the central x-ray beam (20) emanating from an x-ray beam source (19) at a right angle through the desired target view area (23) or (24) so as to contact the midpoint of the properly positioned x-ray film packet (17).

FIG. 9 illustrates the technique for obtaining x-ray film views of the anterior portion of the lower jaw (27) illustrated containing a cyst (25). Referring to the above paragraph describing the basic technique for utilizing this invention, the x-ray film views are obtained by placing the x-ray film packet (17) in a proper position in an x-ray film packet retaining device slot (8) or (9) located in the x-ray film positioner body (A) which is then adjusted and fixed in proper position; then directing the central x-ray beam (20), emanating from an x-ray beam source (19), at a right angle through the desired target view area (25) so as to contact the mid-point of the properly positioned x-ray film packet (17).

FIG. 10 illustrates the technique for obtaining x-ray film views of the posterior portion of the lower jaw (27) containing an illustrated impacted tooth (26). Referring to the above paragraph describing the basic technique for utilizing this invention, the x-ray film packet (17) is placed in a proper position in either x-ray film packet retaining device slot (15) or (16) FIG. 7 contained in an x-ray film packet holding rod device (B) which is placed in proper position; then directing the central x-ray beam (20), emanating from an x-ray beam source (19), through the desired target view area at a right angle to the x-ray film packet's (17) horizontal plane and at such an angle vertically so as to pass under the ipsilateral lower border of the jaw bone (27) so as to contact the midpoint of the properly positioned x-ray film packet (17).

FIG. 11 illustrates the technique for obtaining x-ray film views of the temporomandibular joint (28). Referring to the above paragraph describing the basic technique for utilizing this invention, the x-ray film packet (17) is placed in a proper position in either x-ray film packet retaining device slot (15) or (16) FIG. 7 contained in an x-ray film packet holding rod device (B) which is placed in proper position; then directing the central x-ray beam (20), emanating from an x-ray beam source (19), at an appropriate well-known textbook described angle so as to pass through the center of said joint (28) so as to make contact with the mid-point of the x-ray film packet (17).

The hereinabove description and disclosure represents the preferred exemplary embodiments of the invention which are incorporated in the description of each embodiment whether or not so stated.

Variations of this invention as to form, size, construction, material and configuration of the various components or parts of components thereof are possible without departing from the spirit and scope of the appended claims.

The inventor claims:

1. A device for positioning an x-ray film packet exteriorly of a person's head being photographed in the area of the mouth, comprising: a body having an opening in a first surface thereof for receiving bite platform means adapted to be held between the person's teeth; first attaching means for holding said bite platform means in said body, said first attaching means permitting said body and said bite platform means to be held at a variety of angles with respect to each other; a circular hole passing through said body, a circular rod received in said hole, said rod and said hole being dimensioned to permit said rod to slide through said body and to rotate with respect to said body, second attaching means for holding said rod in a variety of angles and locations with respect to said body; a slit in an end of said rod dimensioned to frictionally engage and hold an edge of an x-ray film packet, said slit permitting said x-ray film packet to be held at a variety of angles with respect to said rod; whereas the various elements cooperate such that (a) adjustment of said angle of said body with respect to said bite platform means, and (b) adjustment of said angle of said x-ray film packet with respect to said slit, and (c) rotation of said rod in said hole, and (d) sliding of said rod through said body, enable saidi x-ray film packet to be essentially universally movable with respect to said mouth area of said person being photographed.

2. The invention defined in claim 1, further comprising a slit in each opposite end of said rod.

3. The invention defined in claim 1, further comprising continuous elongated slot extending the entire length of said rod, said elongated slot being dimensioned to fricitionally engage and hold an edge of an x-ray film packet in said rod.

4. The invention defined in claim 1, further comprising a slot passing through a second surface of said body, said slot being dimensioned to frictionally engage and hold an edge of said x-ray film packet in said body.

5. The invention defined in claim 4, further comprising plurality of slots located in planes which intersect.

6. The invention defined in claim 1, wherein said first and second attaching means are both threaded members passing through threaded holes in said body.

* * * * *